United States Patent [19]
Haber et al.

[11] Patent Number: 5,634,906
[45] Date of Patent: Jun. 3, 1997

[54] NEEDLE HIDING SHIELD FOR A DOSE METERING SYRINGE

[75] Inventors: Terry M. Haber, El Toro; William H. Smedley, Lake Elsinore; Clark B. Foster, Laguna Niguel, all of Calif.

[73] Assignee: Habley Medical Technology Corporation, Lake Forest, Calif.

[21] Appl. No.: 579,369

[22] Filed: Dec. 27, 1995

[51] Int. Cl.⁶ .................................................. A61M 5/20
[52] U.S. Cl. ........................... 604/136; 604/157; 604/198
[58] Field of Search ................................. 604/263, 198, 604/192, 195, 134–137, 110, 187, 232, 207, 157, 156

[56] References Cited

U.S. PATENT DOCUMENTS

| | | | |
|---|---|---|---|
| 5,201,720 | 4/1993 | Borgia et al. | 604/198 |
| 5,358,489 | 10/1994 | Wyrick | 604/136 |
| 5,364,362 | 11/1994 | Schulz | 604/198 X |
| 5,480,387 | 1/1996 | Gabriel et al. | 604/136 X |

*Primary Examiner*—John D. Yasko
*Attorney, Agent, or Firm*—Morland C. Fischer

[57] ABSTRACT

A needle hiding shield to be coupled to a conventional dose metering syringe to hide a hypodermic needle from view of a patient (e.g. a child) to whom an injection is to be administered so as to minimize the anxiety that will be experienced by the patient. According to a first embodiment, the needle hiding shield includes an inner anchoring sleeve that surrounds a medication cartridge housing and an opaque outer sleeve guard that shields a hypodermic needle and is coaxially aligned with and coupled to the inner anchoring sleeve by a pair of springs. An injection is administered when the medication cartridge housing is advanced distally through the outer sleeve guard to cause the springs to be stretched and the needle to be moved outwardly of the outer sleeve guard to penetrate the targeted injection site. According to a second embodiment, the needle hiding shield includes an outer spring sleeve that surrounds the medication cartridge housing in spaced coaxial alignment therewith and is adapted to slide over an opaque inner needle guard that is attached to the outer spring sleeve to shield the hypodermic needle. A coil spring surrounds the medication cartridge housing inside the outer spring sleeve. An injection is administered when the medication cartridge housing is advanced distally into the inner needle guard to cause the outer spring sleeve to slide over the inner needle guard, so that the coil spring is compressed and the needle is moved outwardly from the inner needle guard to penetrate the targeted injection site.

15 Claims, 6 Drawing Sheets

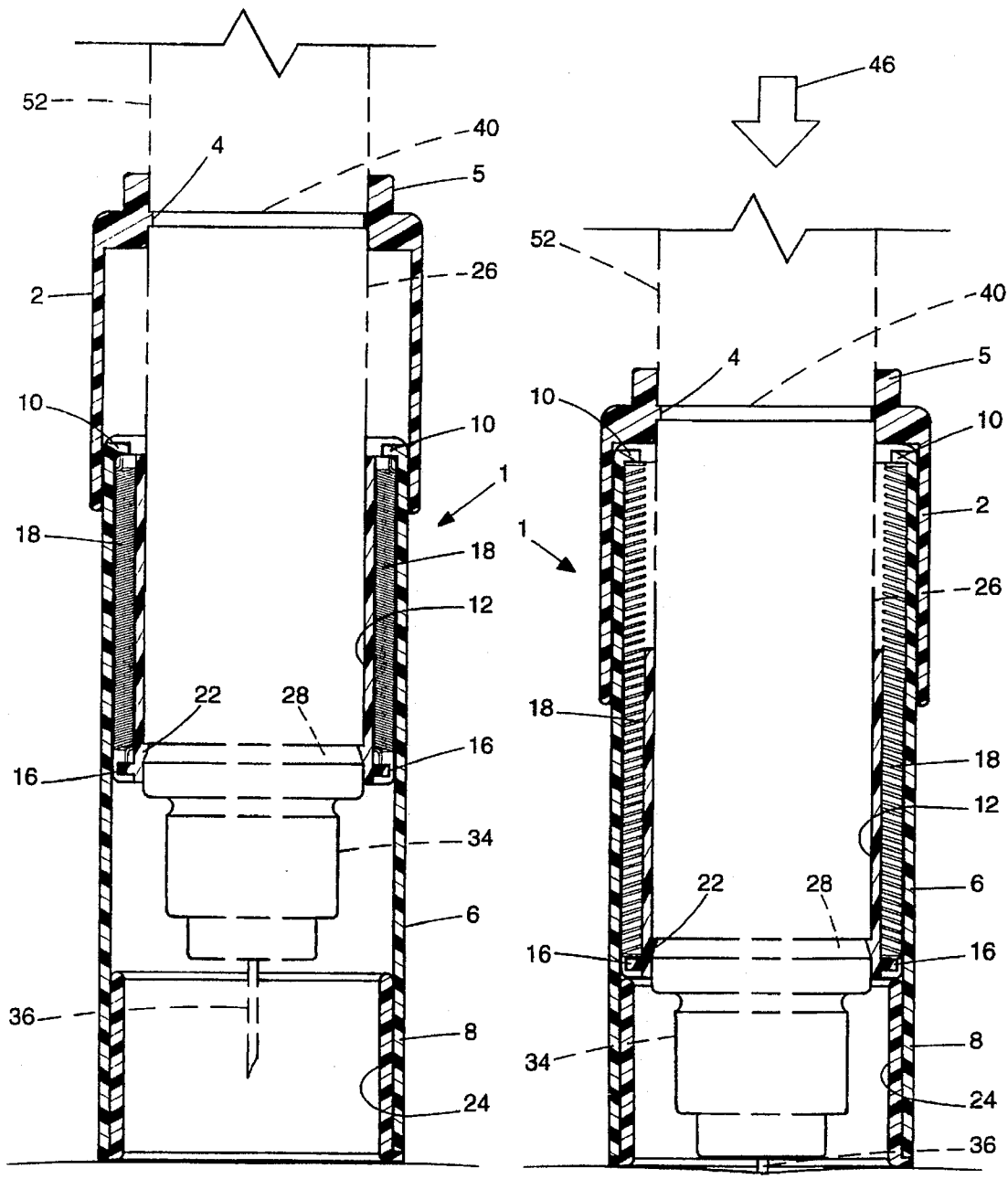

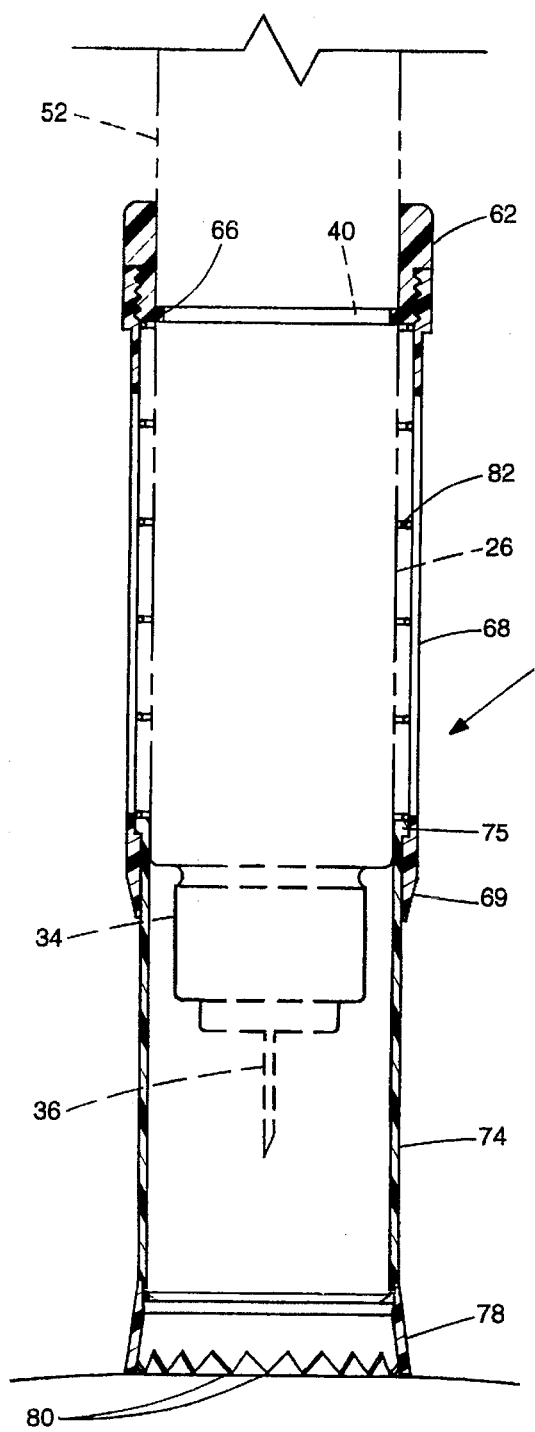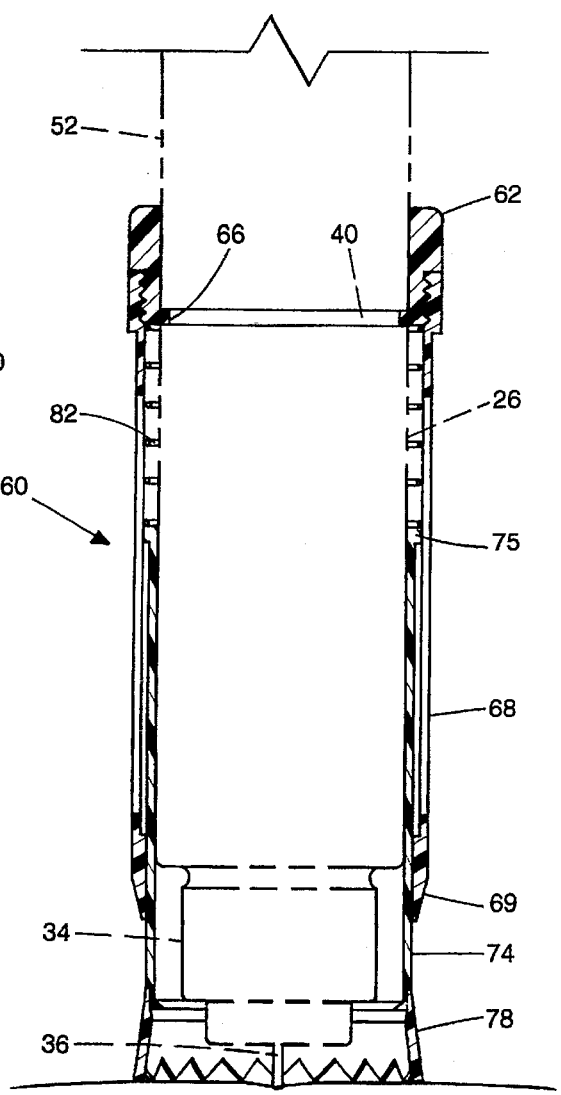
*Fig. 7*  *Fig. 8*

1

NEEDLE HIDING SHIELD FOR A DOSE METERING SYRINGE

BACKGROUND OF THE INVENTION

1. Field of the Invention

This invention relates to a retractable needle shield to be coupled to a conventional dose metering syringe to hide a hypodermic needle from view of a patient to whom an injection is to be administered so as to minimize the anxiety that will be experienced by the patient.

2. Background Art

A dose metering syringe is a commercially available device by which a precise volume of a rare and/or expensive medication or pharmaceutical that is stored in a medication cartridge can be delivered to a patient via a hypodermic needle. Dose metering syringes are often used to administer an injection to a child. For example, in the case where the medication to be delivered is a growth hormone, an injection is typically administered twice a week for approximately two years. As a consequence of the frequency of the injections, the child may become traumatized whenever he sees a hypodermic needle in advance of the needle strike. Such trauma may, over time, subject the child to increased anxiety and a constant fear of all syringes and the hypodermic needles associated therewith.

Accordingly, it would be desirable to be able to shield the hypodermic needle from view of a patient (e.g. a child) so as to reduce the trauma and anxiety that will be experienced by the patient when the dose metering syringe is located at the targeted injection site. However, the foregoing must be accomplished while requiring that only a few or no modifications be made to the syringe. Moreover, the needle shield should be compatible with the hypodermic needles of different manufacturers. In this same regard, one must be able to quickly and easily install the shield on the dose metering syringe as well as remove the shield for cleaning and sterilization. Lastly, the needle must be unshielded to permit the injection to be administered and automatically reshielded at the conclusion of the injection so as to permit a safe handling of the shield while avoiding the possibility of an accidental needle strike.

SUMMARY OF THE INVENTION

A retractable needle shield is disclosed to be coupled to a conventional dose metering syringe to hide a hypodermic needle from view of a patient (e.g. a child) to whom an injection is to be administered so as to reduce the anxiety that will be experienced by the patient. According to a first embodiment, a medication cartridge housing that is coupled to a double ended hypodermic needle and encloses a fluid filled medication cartridge is attached to the main barrel of the dose metering syringe. A finger guard surrounds the distal end of the main barrel and is attached to the cartridge housing. A relatively short inner anchoring sleeve surrounds and engages the cartridge housing. A relatively long outer sleeve guard surrounds the inner anchoring sleeve in spaced, coaxial alignment therewith. A pair of coil springs extends between lower spring posts of the outer sleeve guard and upper spring posts of the inner anchoring sleeve. A travel limit sleeve is frictionally retained within the distal end of the outer sleeve guard to limit the travel of the cartridge housing and the hypodermic needle during the administration of the injection. Either the travel limit sleeve or the distal end of the outer sleeve guard is opaque to hide the needle from view of the patient.

With the needle shield at rest, the springs are in a relaxed state, the cartridge housing and the finger guard are urged to the proximal end of the outer sleeve guard, and the needle is surrounded and shielded by the travel limit sleeve at the distal end of the outer sleeve guard. To administer an injection, an axial pushing force is applied to the medication cartridge housing from the main barrel of the dose metering syringe to cause the cartridge housing and the inner anchoring sleeve attached thereto to move distally through the outer sleeve guard, whereby the finger guard is caused to slide over the sleeve guard and the hypodermic needle is advanced distally and outwardly of the travel limit sleeve to penetrate the targeted injection site. Accordingly, the springs are stressed to store potential energy. At the conclusion of the injection, the springs return to their relaxed state to automatically drive the cartridge housing and the inner anchoring sleeve proximally through the outer sleeve guard so as to withdraw the needle from the injection site to be once again shielded within the travel limit sleeve.

According to a second embodiment, the medication cartridge housing that is coupled to the hypodermic needle and encloses the medication cartridge is again attached to the main barrel of the dose metering syringe. A retaining collar surrounds and is attached to the distal end of the main barrel, and an outer spring sleeve is connected to the retaining collar. An inner needle guard is slidably received through the outer spring sleeve. A single coil spring is located at the interior of the outer spring sleeve in surrounding engagement with the cartridge housing so as to urge the inner needle guard to a position extending outwardly from the distal end of the outer sleeve guard to shield the needle. Attached to the distal end of the inner needle guard is a sensory crown having a set of contact points that engage the targeted tissue site to distract the patient's attention from the needle strike. The inner needle guard is opaque to hide the needle from view of the patient.

With the needle shield at rest, the spring is in a relaxed state, the medication cartridge and the outer spring sleeve are located proximally of the inner needle guard, and the hypodermic needle is surrounded and shielded by the inner needle guard. To administer an injection, an axial pushing force is applied to the medication cartridge housing from the main body of the dose metering syringe to cause the cartridge housing to move distally through the inner needle guard, whereby the outer spring sleeve slides over the inner needle guard and the hypodermic needle is advanced distally and outwardly from the inner needle guard to penetrate the targeted tissue site. Accordingly, the spring is compressed to store potential energy. At the conclusion of the injection, the spring returns to its relaxed state to automatically drive the cartridge housing and the outer spring sleeve proximally relative to the inner needle guard so as to withdraw the needle from the injection site to be once again shielded within the needle guard.

BRIEF DESCRIPTION OF THE DRAWINGS

FIG. 3 shows the needle hiding shield in an at rest condition while surrounding and shielding a hypodermic needle;

FIG. 4 shows the needle hiding shield during the administration of an injection with the hypodermic needle penetrating a targeted injection site;

FIG. 7 shows the needle hiding shield in an at rest condition while surrounding and shielding a hypodermic needle; and FIG. 8 shows the needle hiding shield during the administration of an injection with the hypodermic needle penetrating a targeted injection site.

DETAILED DESCRIPTION

Figure 1:
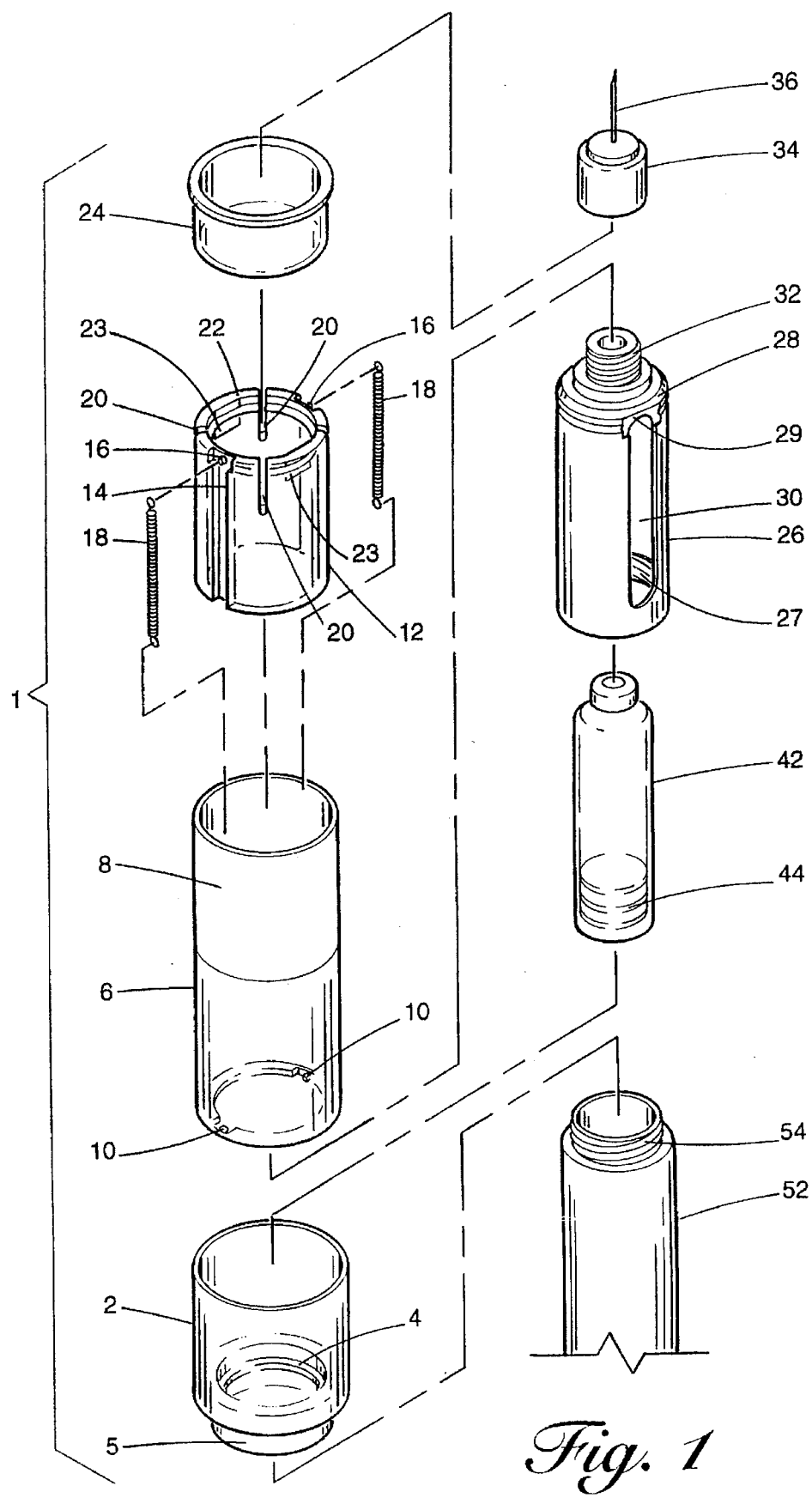
FIG. 1 is an exploded view of a hypodermic needle hiding shield according to a first embodiment of this invention to be coupled to a dose metering syringe.
Figure 2:
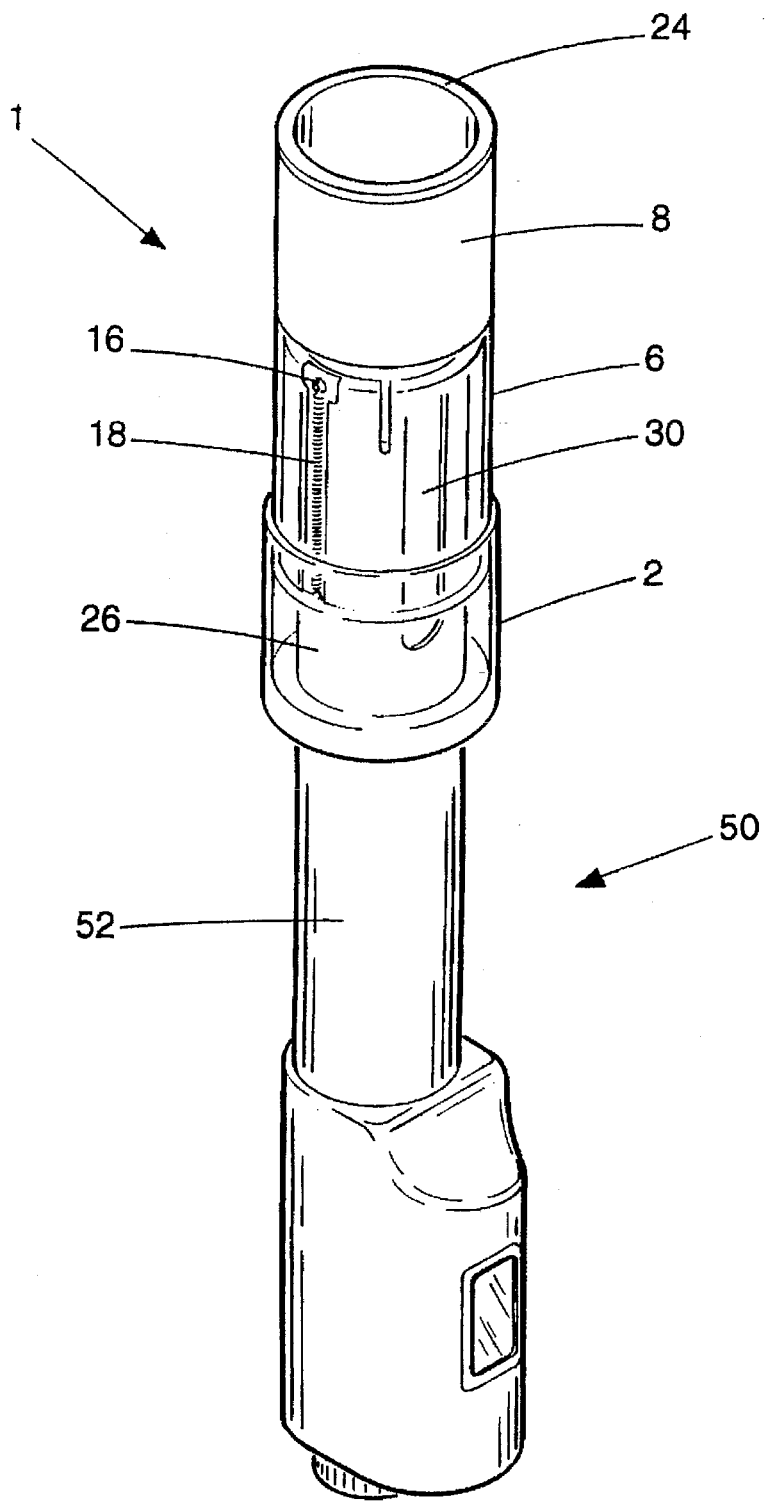
FIG. 2 shows the hypodermic needle hiding shield of FIG. 1 in the assembled relationship coupled to the dose metering syringe.

A hypodermic needle hiding shield 1 which forms a first embodiment of the present invention is best described while referring to the drawings, where FIGS. 1 and 2 show the needle shield in exploded and assembled configurations, respectively, and adapted to be retained at the distal end of the main barrel 52 of a well known, commercially available dose metering syringe 50 (best shown in FIG. 2). Therefore, the construction and operation of the dose metering syringe 50 will not be described herein. By way of example only, the dose metering syringe 50 that is illustrated in the drawings is manufactured by Genentech, Inc. and sold under the trademark GenPen.

The needle hiding shield 1 of the first embodiment includes a cylindrical finger guard 2 that is sized to surround the distal end of the main barrel 52 of dose metering syringe 50. The finger guard is preferably manufactured from clear plastic and includes a radially inward projecting peripheral lip 4 and a relatively narrow proximal collar 5. As is best shown in FIGS. 3 and 4, the peripheral lip 4 of finger guard 2 is retained within an annular gap 40 located between the end-to-end connection of the main barrel 52 and a soon to be described medication cartridge housing 26, while the peripheral collar 5 surrounds and frictionally engages the distal end of the main barrel 52. The purpose of finger guard 2 is to prevent the user of the dose metering syringe 50 from inadvertently grasping the cartridge housing 26 so as to undesirably impede the travel of the cartridge housing 26 relative to an outer sleeve guard 6 during the administration of an injection to a patient (e.g. a child).

The outer sleeve guard 6 is a hollow cylinder that is preferably manufactured from plastic. The proximal end of the outer sleeve guard 6 is transparent, while the distal end 8 thereof may be opaque to obscure the hypodermic needle 36 from view of the patient to whom an injection is to be administered. A pair of opposing lower spring posts 10 projects radially inward towards each other from the proximal end of the outer sleeve guard 6. The diameter of outer sleeve guard 6 is less than the diameter of the finger guard 2, so that in the assembled configuration of FIG. 2, the finger guard 2 surrounds the proximal end of the outer sleeve guard 6 such that sleeve guard 6 is adapted to slide axially along the interior of finger guard 2 for receipt therewithin during the administration of the injection (best shown in FIGS. 3 and 4).

A hollow, cylindrical inner anchoring sleeve 12 is coaxially aligned with and spaced inwardly of the outer sleeve guard 6 so that inner anchoring sleeve 12 surrounds and engages the medication cartridge housing 26 (also best shown in FIGS. 3 and 4). The outer sleeve guard 6 is approximately twice as long as the inner anchoring sleeve 12. Inner anchoring sleeve 12 has a pair of oppositely disposed, longitudinally extending spring receiving grooves 14 (only one of which being visible in FIG. 1). A pair of upper spring posts 16 projects radially outward and away from one another at the distal ends of the spring receiving grooves 14.

A pair of metallic, helically wound coil springs 18 are received in respective ones of the pair of spring receiving grooves 14 formed in inner anchoring sleeve 12. Although the springs 18 have been described herein as metallic coil springs, it is to be understood that other suitable springs, such as elastomeric bands, or the like, may be substituted therefor. In the assembled needle shield configuration of FIG. 2, the helically wound coil springs 18 are connected at opposite ends thereof between the lower spring posts 10 that project radially inward from the proximal end of outer sleeve guard 6 and the upper spring posts 16 that project radially outward from the distal ends of the spring receiving grooves 14 of the inner anchoring sleeve 12.

Inner anchoring sleeve 12 also has a series of longitudinal slots 20 that are arranged in spaced, parallel alignment with one another. The slots 20 allow the inner anchoring sleeve 12 to dilate (i.e. flex) when exposed to an expansive force as might be encountered when sleeve 12 surrounds and engages the medication cartridge housing 26. A circumferential ridge 22 projects radially inward from the distal end of the inner anchoring sleeve 12 to be snap-fit within a peripheral retaining groove 28 of the cartridge housing 26 as will be described in greater detail hereinafter. A pair of short, flat keys 23 extend inwardly of inner anchoring sleeve 12 below the circumferential ridge 22 for a purpose that will also soon be described.

A hollow, cylindrical travel limit sleeve 24 is sized to be frictionally retained within the distal end of the outer sleeve guard 6. Travel limit sleeve 24 is preferably manufactured from either transparent or opaque plastic. In the case where sleeve 24 is opaque (so as to obscure the hypodermic needle 36 from view of the patient), the distal end 8 of outer sleeve guard 6 could be transparent rather than opaque, as earlier disclosed.

The inclusion of travel limit sleeve 24 permits a sufficient axial pushing force to be transferred to the inner anchoring sleeve 12, whereby to move sleeve 12 towards the cartridge housing 26 during assembly of the needle hiding shield 1 so that the circumferential ridge 22 of sleeve 12 will be received by the peripheral retaining groove 28 of cartridge housing 26 so as to cause the inner anchoring sleeve 12 and the cartridge housing 26 to be placed in interlocking engagement with one another. Moreover, with travel limit sleeve 24 retained at the distal end of outer sleeve guard 6, the distal travel of cartridge housing 26 can be limited to permit the hypodermic needle 36 to extend only to its full length necessary for administering the injection.

The medication cartridge housing 26 is of relatively conventional design. That is, cartridge housing 26 has a hollow, cylindrical body that encloses a standard, fluid filled medication cartridge 42. Cartridge housing 26 includes a pair of elongated, oppositely disposed windows 30 by which to enable the administrator of the injection to visually inspect the medication cartridge 42 and the volume of fluid therewithin. The proximal end of the cartridge housing 26 has a set of peripheral screw threads 27 extending around the interior thereof by which to couple cartridge housing 26 to the main barrel 52 at a set of corresponding peripheral screw threads extending around the distal end of main barrel 52. In this regard, and as was earlier disclosed, with the needle hiding shield 1 in the assembled relationship, the cartridge housing 26 and the main barrel 52 are connected end-to-end one another such that the aforementioned annular gap 40 is established therebetween (best shown in FIGS. 3 and 4). As was also earlier disclosed, the peripheral lip 4 of finger guard 2 is received and retained within the annular gap 40, whereby finger guard 4, inner anchoring sleeve 12, cartridge housing 26 and main barrel 52 are all movable with one another during the administration of the injection.

The distal end of cartridge housing 26 tapers to form a relatively narrow screw threaded neck 32. A correspondingly screw threaded needle hub 34 that carries a double ended hypodermic needle 36 (only the distal end of which is visible in FIG. 1) is coupled to the distal end of the main barrel 52 at the screw threaded neck 32 thereof such that in the assembled relationship of FIG. 2, the proximal end of needle 36 will extend inwardly and proximally through medication cartridge housing 26 to be placed in fluid communication with the medication cartridge 42 that is enclosed by the cartridge housing 26.

However, the medication cartridge housing 26 is modified relative to conventional cartridge housings so as to include a peripheral retaining groove 28 extending around the distal end thereof below threaded neck 32 and a small flat 29 located above each of the windows 30. As was earlier described and as is best shown in FIGS. 3 and 4, during assembly of the needle hiding shield 1, the circumferential ridge 22 projecting inwardly from the distal end of the inner anchoring sleeve 12 is moved towards and snap-fit within the peripheral retaining groove 28 of cartridge housing 26 so that the cartridge housing 26 and the sleeve 12 surrounding housing 26 are connected together and movable with one another during the administration of the injection. What is more, the flats 29 receive the respective keys 23 of the inner anchoring sleeve 12 thereagainst so as to prevent a rotation of the cartridge housing 26 and an undesirable relocation of the viewing windows 30 thereof.

The medication cartridge 42 is a well known, fluid filled cartridge in which a medicine or pharmaceutical is stored for delivery to the patient via hypodermic needle 36. The usual piston 44 is located at the proximal end of medication cartridge 42 to be urged therethrough in order to cause the fluid contents of cartridge 42 to be expulsed during the administration of the injection. The cartridge 42 is surrounded by the medication housing 26 so that the volume of fluid remaining in the cartridge is visible through the window 30 of housing 26.

The operation of the needle hiding shield 1 of this embodiment is now described in detail while referring to FIGS. 3 and 4 of the drawings. FIG. 3 shows the needle hiding shield 1 coupled to the main barrel 52 of the dose metering syringe 50 (of FIG. 2) while the shield is at rest. More particularly, the outer sleeve guard 6 of shield 1 is positioned around the targeted injection site of the patient. As earlier disclosed, either the distal end 8 of outer shield guard 6 or the travel limit sleeve 24 located within the distal end 8 of guard 6 is opaque to hide the hypodermic needle 36 from view of the patient to thereby minimize the anxiety to be experienced by the patient in anticipation of the injection.

In the at rest condition of FIG. 3, the hypodermic needle 36 is biased in the shielded or retracted position relative to outer sleeve guard 6 in spaced alignment above the targeted injection site. That is to say, the pair of springs 18 connected between the lower and upper spring posts 10 and 16 are relaxed. The inner anchoring sleeve 12 that surrounds and engages the medication cartridge housing 26 (by means of the receipt of circumferential ridge 22 within peripheral retaining groove 28) is urged by the springs 18 so that cartridge housing 26 is positioned at the proximal end of outer sleeve guard 6. The finger guard 2 that is coupled to cartridge housing 26 (by means of the receipt of peripheral lip 4 within annular gap 40) is therefore also positioned at the proximal end of the outer sleeve guard 6.

When an injection is to be administered, an axial pushing force is applied (in the direction of the reference arrow 46 of FIG. 4) to the main barrel 52. The axial pushing force applied to main barrel 52 is transferred to the medication cartridge housing 26 which in turn moves distally through the outer sleeve guard 6 towards the targeted injection site. Accordingly, the inner anchoring sleeve 12 that is coupled to the cartridge housing 26 at peripheral groove 28 will also move distally through sleeve guard 6 along with cartridge housing 26, whereby to cause the pair of springs 18 to be stretched and thereby store potential energy. Similarly, the finger guard 2 that is coupled to the main barrel 52 moves distally along with cartridge housing 26 and main barrel 52 so as to slidably receive and surround the proximal end of the outer sleeve guard 6 therewithin.

The distal advancement of the medication cartridge housing 26 through the outer sleeve 6 continues until the hypodermic needle 36 coupled to cartridge housing 26 (by means of needle hub 34) penetrates the targeted injection site and the further displacement of cartridge housing 26 is blocked by travel limit sleeve 24. The dose metering syringe 50 (of FIG. 2) may then be operated in the usual fashion so that a precise volume of medication/pharmaceutical is delivered to the patient from the medication cartridge 42 (of FIG. 1) to the targeted injection site via needle 36.

When the injection has been completed and the axial pushing force (represented by reference arrow 46) being applied to the main barrel 52 and the medication cartridge 26 is terminated, the potential energy stored by springs 18 automatically returns the needle hiding shield 1 to the at rest condition of FIG. 3. That is, the inner anchoring sleeve 12 and the medication cartridge housing 26 coupled thereto are simultaneously driven proximally through the outer sleeve guard 6, so that the hypodermic needle 36 will be withdrawn from the injection site and once again shielded by the outer sleeve guard 6 as the springs 18 return to their original relaxed state. The finger guard 2 is driven proximally along with cartridge housing 26 so as to slide over the outer sleeve guard 6 to the proximal end thereof. The dose metering syringe 50 and the needle hiding shield 1 coupled thereto may then be removed from the patient for cleaning and/or removal of the medication cartridge 42, whereupon the process for administering the injection is completed while the patient experiences less emotional trauma as a result of not being able to see the injection taking place.

Figure 5:
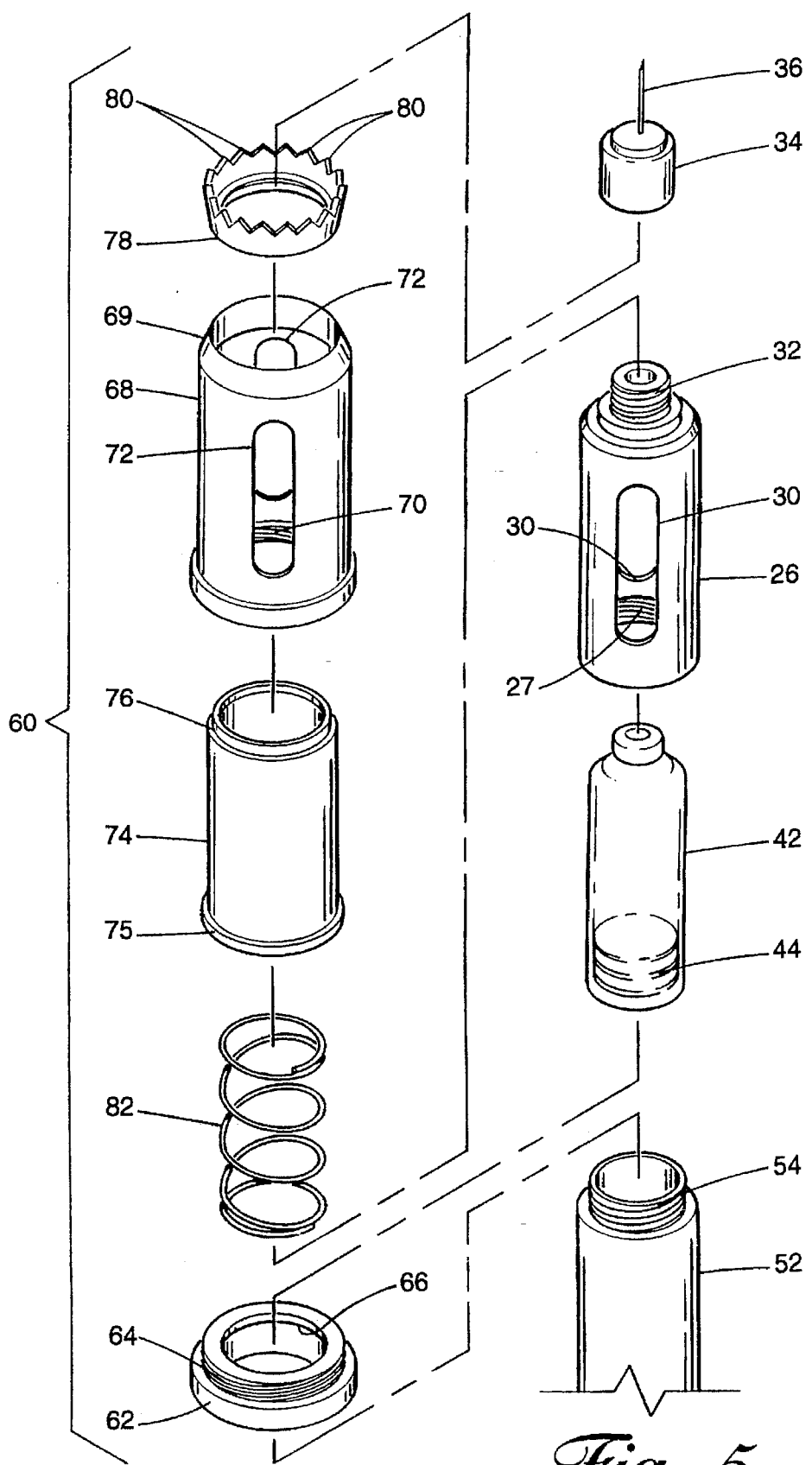
FIG. 5 is an exploded view of a hypodermic needle hiding shield according to a second embodiment of this invention to be coupled to a dose metering syringe.
Figure 6:
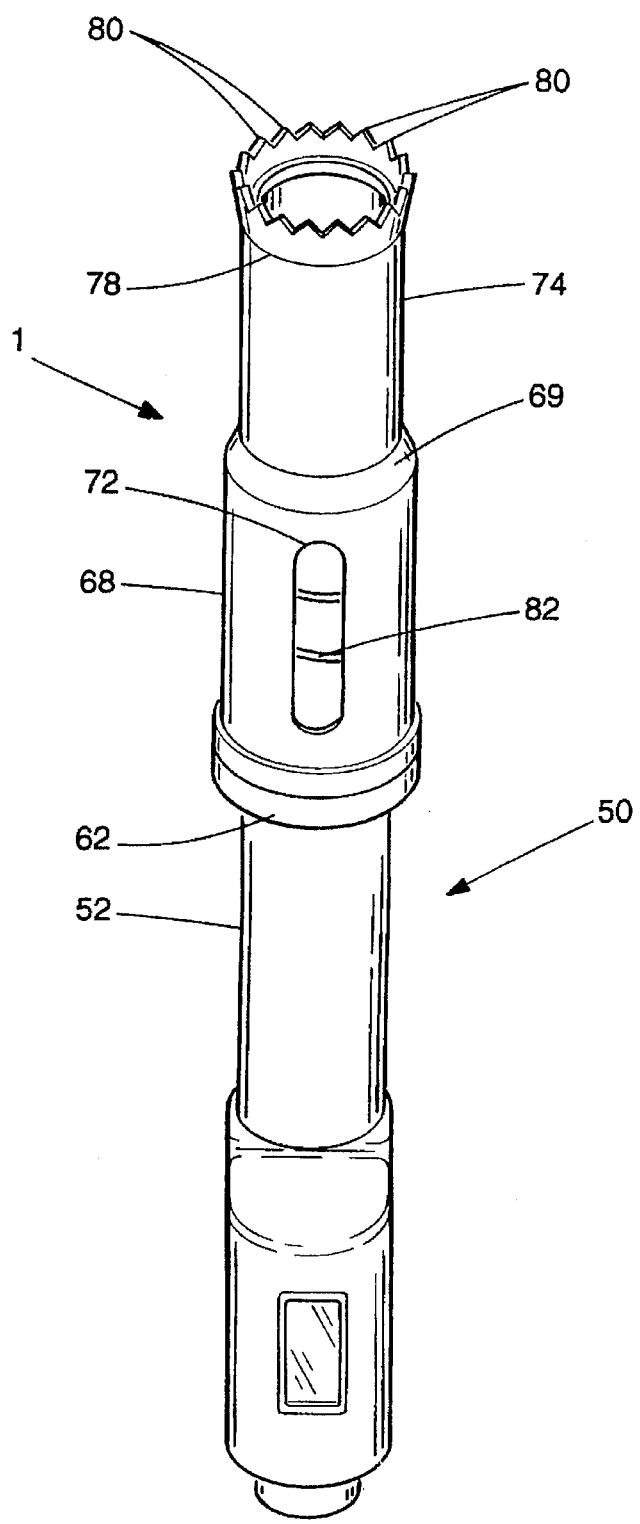
FIG. 6 shows the needle hiding shield of FIG. 5 in the assembled relationship coupled to the dose metering syringe.

A hypodermic needle hiding shield 60 which forms a second embodiment of the present invention is initially described while referring to FIGS. 5 and 6 of the drawings where the needle shield is shown in exploded and assembled configurations, respectively. The needle hiding shield 1 of this embodiment is adapted to be retained at the distal end of the main barrel 52 of the same dose metering syringe 50 to which the needle hiding shield 1 of FIGS. 1–4 was coupled in the manner that has been described above.

The needle hiding shield 60 of the second embodiment includes a retaining collar 62 having a set of screw threads 64 extending around the exterior thereof. The retaining collar 62 is sized to surround and frictionally engage the distal end of the main barrel 52 of dose metering syringe 50 (of FIG. 6). The retaining collar 62 includes a radially inward projecting peripheral lip 66 to be received within the annular gap 40 that is established when the main barrel 52 and the medication cartridge 26 are connected end-to-end one another (as is best shown in FIGS. 7 and 8).

Needle shield 60 also includes a hollow, generally cylindrical outer spring sleeve 68. Spring sleeve 68 has an inwardly tapered distal end 69 and a set of internal screw threads 70 extending around the proximal end thereof. A pair of elongated, oppositely disposed windows 72 are formed through outer spring sleeve 68 to enable the administrator of the injection to visually inspect the volume of fluid in the medication cartridge 42. When the needle hiding shield 60 is coupled to the dose metering syringe 50 (as shown in FIG. 6), the set of screw threads 70 at the proximal end of outer spring sleeve 68 is mated to the set of screw threads 64 of retaining collar 62, whereupon the outer spring sleeve 68 and the retaining collar 62 are connected together.

A hollow cylindrical inner needle guard 74 has a diameter that is slightly less than the diameter of outer spring sleeve 68 so that during the assembly of needle shield 60, the inner needle guard 74 will slide axially and distally through outer spring sleeve 68. To this end, a relatively wide peripheral flange 75 is formed around the proximal end of the inner needle guard 74 to cooperate with the inwardly tapered distal end 69 of the outer spring sleeve 68 in order to prevent the needle guard 74 from sliding outwardly through and becoming detached from the distal end of spring sleeve 68. It is preferable that inner needle guard 74 be manufactured from an opaque plastic so that during the administration of the injection, the needle guard 74 will hide the hypodermic needle 36 from view of the patient to whom the injection is to be administered.

A relatively narrow peripheral channel 76 is formed around the distal end of the inner needle guard 74. With the inner needle guard 74 moved through and projecting outwardly from the outer spring sleeve 68 (best shown in FIG. 6), a sensory crown 78 is affixed (e.g. glued on or press fit) to the needle guard 74 at the peripheral channel 76 thereof. A plurality of evenly spaced contact points (e.g. tangs) 80 extends distally from the sensory crown 78. During the administration of the injection, the contact points 80 of sensory crown 78 will surround the targeted injection site (best shown in FIGS. 7 and 8) so as to confuse the senses of the patient and distract the patient's attention away from the actual needle strike point to thereby minimize patient discomfort.

Instead of a pair of coil springs (designated 18 in FIG. 1), the needle hiding shield 60 includes a single, metallic helically wound coil spring 82. In the assembled relationship, coil spring 82 is located at the interior of the outer spring sleeve 68 in surrounding engagement with the medication cartridge housing 26 so as to extend between the retaining collar 62 at the proximal end of spring sleeve 68 and the inner needle guard 74 at the distal end of spring sleeve 68.

The needle hiding shield 60 of this embodiment is adapted to be interfaced with a medication cartridge housing 26 that encloses a fluid filled medication cartridge 42, a double ended hypodermic needle 36 that is carried by a needle hub 34, and the medication cartridge 42 having the usual piston 44 and storing therewithin a medication or pharmaceutical to be delivered to the patient during the injection. Since the medication cartridge housing 26, hypodermic needle 36, and medication cartridge 42 of this embodiment are substantially identical to those already described above, the same reference numerals have been used. Therefore, these components will not be described again, except to say that the set of screw threads 27 at the proximal end of cartridge housing 26 is mated to the screw threads 54 at the distal end of the main barrel 52 so that the retaining collar 62 will be retained between main barrel 52 and cartridge housing 26 (best shown in FIGS. 7 and 8). In addition, needle hub 34 is attached to the medication cartridge housing 26 at a screw threaded neck 32 of the cartridge housing so that the proximal end of the needle 36 can be placed in fluid communication with the medication cartridge 42 enclosed by housing 26.

However, it is pointed out that the medication cartridge housing 26 of this embodiment is a well known, commercially available device. Therefore, and unlike the cartridge housing 26 shown in FIG. 1, the cartridge housing 26 of FIG. 5 is devoid of the peripheral retaining groove 28 and the flats 29, such that the cartridge housing 26 of FIG. 5 advantageously requires no modifications to be interfaced with the needle hiding shield 60.

The operation of the needle hiding shield 60 of this embodiment is now disclosed in detail while referring to FIGS. 7 and 8 of the drawings. FIG. 7 shows the needle hiding shield 60 coupled to the main barrel 52 of the dose metering syringe 50 (of FIG. 6) while the shield is at rest. More particularly, the inner needle guard 74 of shield 60 is positioned around the targeted injection site of the patient so that the contact points 80 of sensory crown 78 engage the patient's skin for the advantage described above. As earlier disclosed, the inner needle guard 74 is opaque to hide the hypodermic needle 36 from view of the patient to thereby minimize the anxiety to be experienced by the patient in anticipation of the injection.

In the at rest condition of FIG. 7, the hypodermic needle 36 is biased in the shielded or retracted position relative to inner needle guard 74 in spaced alignment above the targeted injection site. That is to say, the spring 82 located at the interior of outer spring sleeve 68 in surrounding engagement with the medication cartridge housing 26 is in a relaxed state between retaining collar 62 and inner needle guard 74. Therefore, the inner needle guard 74 is urged to a position extending outwardly and distally from the outer spring sleeve 68 for engagement with the targeted injection site.

When an injection is to be administered, an axial pushing force is applied (in the direction of the reference arrow 82 of FIG. 8) to the main barrel 52. The axial pushing force applied to the main barrel 52 is transferred to the medication cartridge housing 26 which in turn moves distally through the inner needle guard 74 towards the injection site. Since the retaining collar 62 is connected to the cartridge housing 26 (by means of the peripheral lip 66 thereof being received at the annular gap 40 between cartridge housing 26 and main barrel 52) and to the outer spring sleeve 68, the outer spring sleeve 68 will move distally with cartridge housing 26 so as to slide over the inner needle guard 74 towards the injection site. Accordingly, the spring 82 is compressed between the retaining collar 62 and the inner needle guard 74 so as to store potential energy.

The distal advancement of the medication cartridge housing 26 through the inner needle guard 74 continues until the hypodermic needle 36 coupled to cartridge housing 26 (by means of needle hub 34) penetrates the targeted injection site. The dose metering syringe 50 (of FIG. 6) may then be operated in the usual fashion so that a precise volume of medication/pharmaceutical is delivered to the patient from the medication cartridge 42 (of FIG. 5) to the targeted injection site via needle 36.

When the injection has been completed and the axial pushing force (represented by reference arrow 84) being applied to the main barrel 52 and the medication cartridge 26 is terminated, the potential energy stored by spring 82 automatically returns the needle hiding shield 60 to the at rest condition of FIG. 7. That is, the retaining collar 62 as well as the medication cartridge housing 26 and the outer spring sleeve 68 are simultaneously driven proximally relative to inner needle guard 74, whereby the hypodermic needle 36 will be withdrawn from the injection site and once again shielded by the inner needle guard 74 as the spring 82 returns to its original relaxed state. The dose metering syringe 50 and the needle hiding shield 60 coupled thereto may then be removed from the patient, whereupon the process for administering the injection is completed while the patient experiences less emotional trauma as a result of not being able to see the injection taking place.

It will be apparent that while the preferred embodiments of the invention have been shown and described, various modifications and changes may be made without departing from the true spirit and scope of the invention.

Having thus set forth the preferred embodiments, what is claimed is:

1. In combination:
   a syringe to administer an injection, said syringe having a medication cartridge in which a fluid medication is stored, a medication cartridge housing enclosing said medication cartridge, and a hypodermic needle coupled to said medication cartridge housing to communicate fluidically with said medication cartridge; and
   a needle hiding shield to shield the hypodermic needle from view of a patient to whom the injection is to be administered, said needle hiding shield comprising:
   a cylindrical inner sleeve surrounding said medication cartridge and attached thereto,
   a cylindrical outer sleeve guard having proximal and distal ends, the proximal end of said outer sleeve guard surrounding said inner sleeve and the distal end of said outer sleeve guard surrounding and shielding said hypodermic needle, and
   spring means extending between said inner sleeve and said outer sleeve guard,
   said medication cartridge housing and said inner sleeve attached thereto advancing distally through said outer sleeve guard when the injection is administered to cause said spring means to be stretched and said hypodermic needle to be moved outwardly from the distal end of said outer sleeve guard to penetrate an injection site at which to deliver the fluid medication from said medication cartridge, said spring means relaxing at the conclusion of the injection to drive said medication cartridge housing and said inner sleeve attached thereto proximally through said outer sleeve guard whereupon to retract said hypodermic needle inwardly of the distal end of said outer sleeve guard to be reshielded thereby.

2. The combination recited in claim 1, wherein said inner sleeve and said outer sleeve guard are arranged in coaxial alignment with one another and said spring means having first and opposite ends, the first end of said spring means connected to said inner sleeve and the opposite end of said spring means connected to the proximal end of said outer sleeve guard, such that said spring means is stretched when said medication cartridge housing and said inner sleeve attached thereto advance distally through said outer sleeve guard during the administration of the injection.

3. The combination recited in claim 1, wherein said inner sleeve has at least one longitudinally extending spring receiving groove formed therein, said spring means received within said at least one spring receiving groove.

4. The combination recited in claim 1, wherein said inner sleeve has a circumferential ridge projecting inwardly thereof and said medication cartridge housing has a peripheral retaining groove extending therearound, said circumferential ridge received within said peripheral retaining groove to attach said inner sleeve to said medication cartridge housing such that said inner sleeve and said medication cartridge housing move together through said outer sleeve guard.

5. The combination recited in claim 1, wherein said outer sleeve guard is longer than said inner sleeve.

6. The combination recited in claim 1, wherein at least the distal end of said outer sleeve guard is opaque to hide said hypodermic needle from view of the patient when said hypodermic needle is surrounded and shielded by the distal end of said outer sleeve guard.

7. The combination recited in claim 1, further comprising a hollow travel limit sleeve retained inside the distal end of said outer sleeve guard, said travel limit sleeve blocking the distal advancement of said medication cartridge housing through said outer sleeve guard during the administration of the injection after said hypodermic needle moves outwardly from the distal end of said outer sleeve guard and penetrates the injection site.

8. The combination recited in claim 7, wherein said travel limit sleeve is opaque to hide said hypodermic needle from view of the patient when said hypodermic needle is surrounded and shielded by the distal end of said outer sleeve guard.

9. The combination recited in claim 1, further comprising a hollow finger guard located at the proximal end of said outer sleeve guard and coupled to said medication cartridge housing in surrounding engagement therewith to prevent manual access to said medication cartridge housing, said finger guard advancing distally with said medication cartridge housing during the administration of the injection to slide over and receive the proximal end of said outer sleeve guard therewithin.

10. The combination recited in claim 9, wherein said finger guard includes a peripheral lip projecting inwardly thereof, said peripheral lip contacting said medication cartridge housing whereby said finger guard engages said medication cartridge housing so as to advance therewith during the administration of the injection.

11. In combination:
    a syringe to administer an injection, said syringe having a medication cartridge in which a fluid medication is stored, a medication cartridge housing enclosing said medication housing, and a hypodermic needle coupled to said medication cartridge housing to communicate fluidically with said medication cartridge; and
    a needle hiding shield to shield the hypodermic needle from view of a patient to whom the injection is to be administered, said needle hiding shield comprising:
    a cylindrical outer spring sleeve having proximal and distal ends, said outer spring sleeve surrounding said medication cartridge housing in spaced coaxial alignment therewith,
    a cylindrical inner needle guard extending outwardly from the distal end of said outer spring sleeve so that said outer spring sleeve is adapted to slide over said inner needle guard, said inner guard surrounding and shielding said hypodermic needle,
    a retaining collar connected to the proximal end of said outer spring sleeve, said retaining collar coupled to said medication cartridge housing so that said outer spring sleeve is interconnected to and movable with said medication cartridge housing, and spring means surrounded by said outer spring sleeve and extending between said retaining collar at the proximal end of said outer spring sleeve and said inner needle guard at the distal end of said outer spring sleeve, said medication cartridge housing and said outer spring sleeve being responsive to a distal force generated by said syringe such that said outer spring sleeve slides distally over said inner needle guard to cause said spring means to be compressed between said retaining collar and said inner needle guard and said medication cartridge housing advances distally through said outer spring sleeve and into said inner needle guard whereby said hypodermic needle projects outwardly from said inner needle guard to penetrate an injection site at which to deliver the fluid medication from said medication cartridge, said spring means relaxing at the conclusion of the injection to cause said outer spring sleeve to slide proximally over said inner needle guard and said medication cartridge housing to move proximally relative to said inner needle guard whereupon to retract said hypodermic needle inwardly of said inner needle guard to be reshielded thereby.

12. The combination recited in claim 11, wherein said spring means is a coil spring that surrounds said medication cartridge housing.

13. The combination recited in claim 11, wherein said inner needle guard is opaque to hide said hypodermic needle from view of the patient when said hypodermic needle is surrounded by said inner needle guard.

14. The combination recited in claim 11, further comprising a sensory crown attached to and projecting from said inner needle guard to surround the injection site during the administration of the injection, said sensory crown having a plurality of contact points to engage the patient's skin and thereby distract the patient's attention when said hypodermic needle penetrates the injection site.

15. The combination recited in claim 11, wherein said retaining collar surrounds said medication cartridge housing and includes a peripheral lip projecting inwardly thereof, said peripheral lip contacting said medication cartridge housing whereby said retaining collar is coupled to said medication cartridge housing and said outer spring sleeve is interconnected to and movable with said medication cartridge housing.

* * * * *